US008213005B2

(12) United States Patent
Masilamani et al.

(10) Patent No.: US 8,213,005 B2
(45) Date of Patent: Jul. 3, 2012

(54) METHOD FOR DISCRIMINATING BETWEEN BENIGN AND MALIGNANT PROSTATE TUMORS

(75) Inventors: Vadivel Masilamani, Riyadh (SA); Danny M. Rabah, Riyadh (SA); Mohamad Saleh Alsalhi, Riyadh (SA)

(73) Assignee: King Saud University, Riyadh (SA)

( * ) Notice: Subject to any disclaimer, the term of this patent is extended or adjusted under 35 U.S.C. 154(b) by 388 days.

(21) Appl. No.: 12/654,782

(22) Filed: Dec. 31, 2009

(65) Prior Publication Data

US 2010/0173350 A1 Jul. 8, 2010

Related U.S. Application Data (63) Continuation-in-part of application No. 12/591,749, filed on Nov. 30, 2009, which is a continuation-in-part of application No. 12/458,489, filed on Jul. 14, 2009, now abandoned, application No. 12/654,782, which is a continuation-in-part of application No. 12/285,670, filed on Oct. 10, 2008, now Pat. No. 7,869,033, which is a continuation-in-part of application No. 12/000,233, filed on Dec. 11, 2007, now abandoned, which is a continuation-in-part of application No. 11/017,913, filed on Dec. 22, 2004, now abandoned.

(60) Provisional application No. 61/129,728, filed on Jul. 15, 2008, provisional application No. 60/531,987, filed on Dec. 24, 2003.

(51) Int. Cl.
*G01J 3/30* (2006.01)
(52) U.S. Cl. ........................................ 356/317
(58) Field of Classification Search .................. 356/317; 600/317
See application file for complete search history.

(56) References Cited

U.S. PATENT DOCUMENTS

| 4,541,438 A | 9/1985 | Parker et al. |
| 4,933,274 A | 6/1990 | Sanford et al. |
| 5,131,398 A | 7/1992 | Alfano et al. |
| 5,270,171 A | 12/1993 | Cercek et al. |
| 5,422,093 A | 6/1995 | Kennedy et al. |
| 5,579,773 A | 12/1996 | Vo-Dinh et al. |
| 5,769,081 A * | 6/1998 | Alfano et al. ............ 600/476 |
| 6,080,584 A | 6/2000 | Alfano et al. |

(Continued)

FOREIGN PATENT DOCUMENTS

CN 101334399 A 12/2008

(Continued)

OTHER PUBLICATIONS

Katz et al., "Optical Biopsy-Detecting Cancer with Light", 1996, OSA TOPS on Biomedical Optical Spectroscopy and Diagnostics, vol. #, pp. 132-135.*

(Continued)

*Primary Examiner* — Kara E Geisel
(74) *Attorney, Agent, or Firm* — Richard C. Litman (57) ABSTRACT

The method for discriminating between benign and malignant prostate tumors relates to analyzing samples of blood, urine and tissue by fluorescence spectroscopy in order to detect the presence of naturally occurring molecules in the fluids and tissue that serve as biomarkers indicative of cancer in the human body. The analysis can be carried out based on fluorescence emission spectra, fluorescence excitation spectra and synchronous (emission and excitation) spectra of biosamples. The detection, diagnosis, and follow-up and also discrimination between malignant and benign prostate tumors may be made by comparison of ratios of fluorescence emissions and/or excitation intensities of tryptophan, tyrosine, elastin, collagen, bile pigments, NADH, flavins and various species of porphyrins.

1 Claim, 11 Drawing Sheets

U.S. PATENT DOCUMENTS

| | | | |
|---|---|---|---|
| 6,083,487 | A | 7/2000 | Biel |
| 6,091,985 | A | 7/2000 | Alfano et al. |
| 6,256,530 | B1 | 7/2001 | Wolfe |
| 6,316,215 | B1 | 11/2001 | Adair et al. |
| 6,696,241 | B2 | 2/2004 | Thompson et al. |
| 6,750,037 | B2 | 6/2004 | Adair et al. |
| 6,885,440 | B2 * | 4/2005 | Silcott et al. .......... 356/73 |
| 6,905,880 | B1 | 6/2005 | Schwertner |
| 6,984,498 | B2 | 1/2006 | Adair |
| 7,192,783 | B2 * | 3/2007 | Alfano et al. .......... 436/171 |
| 2002/0115121 | A1 | 8/2002 | Garwin |
| 2003/0158470 | A1 * | 8/2003 | Wolters et al. .......... 600/317 |
| 2004/0202612 | A1 | 10/2004 | Adair |
| 2007/0129613 | A1 | 6/2007 | Rochester et al. |
| 2009/0046286 | A1 | 2/2009 | Masilamani et al. |

FOREIGN PATENT DOCUMENTS

| | | |
|---|---|---|
| CN | 101344525 A | 1/2009 |
| WO | WO2009074275 A1 | 6/2009 |

OTHER PUBLICATIONS

Madhuri et al., "Ultraviolet Fluorescence Spectroscopy of Blood Plasma in the Discrimination of Cancer from Normal", 1997, SPIE, vol. 2982, pp. 41-45.*

Kalaivani et al., "Fluorescence Spectra of Blood Components for Breast Cancer Diagnosis", 2008, Photomedicine and Laser Surgery, vol. 26, No. 3, pp. 251-256.*

* cited by examiner

METHOD FOR DISCRIMINATING BETWEEN BENIGN AND MALIGNANT PROSTATE TUMORS

CROSS-REFERENCE TO RELATED APPLICATIONS

This application is a continuation-in-part of U.S. patent application Ser. No. 12/591,749, filed Nov. 30, 2009, which is a continuation-in-part of U.S. patent application Ser. No. 12/458,489, filed Jul. 14, 2009 now abandoned, which claims priority to U.S. provisional patent application Ser. No. 61/129,728, filed Jul. 15, 2008. This application is also a continuation-in-part of U.S. patent application Ser. No. 12/285,670, filed Oct. 10, 2008 now U.S. Pat. No. 7,869,033, which is a continuation-in-part of U.S. patent application Ser. No. 12/000,233, filed Dec. 11, 2007, now abandoned, which is a continuation-in-part of U.S. patent application Ser. No. 11/017,913, filed Dec. 22, 2004, now abandoned, which claims priority to U.S. provisional patent application 60/531,987, filed Dec. 24, 2003. This application also claims priority to India patent application number 587/CHE/2003, filed Jul. 22, 2003 and issued as India patent number 209084 on Aug. 20, 2007.

BACKGROUND OF THE INVENTION

1. Field of the Invention

The present invention relates to the diagnosis and discrimination of cancerous tumors, and particularly to a method for discriminating between benign and malignant prostate tumors that uses fluorescence spectroscopy to examine samples of blood, urine, and/or tissue to diagnose cancer of the prostate during pre-malignant, early malignant, and advanced malignancy stages, and more particularly, aids in discrimination between prostate cancer (CaP) and benign prostate hyperplasia (BPH).

2. Description of the Related Art

Cancer is often a fatal disease. Modern medicine has developed many modes of treating cancer, including surgical removal of tumors, chemotherapy, immunological therapy, etc. However, the key to effective treatment is early detection. A number of diagnostic tests are available for determining the presence of cancer. These tests include: surgical biopsy; prostate specific antigen (PSA); DRE tests; computed axial tomography (CAT or CT scans); magnetic resonance imaging (MRI) scans; ultrasound scans; bone scans; positron emission tomography (PET) scans; bone marrow testing; barium swallow tests; endoscopy; cytoscopy; T/Tn antigen tests; mammography; and other tests. Although effective to a greater or lesser extent, each of these tests has both advantages and disadvantages.

Some tests, such as PSA, pap smears, and mammography, are specific to particular organs. Others, such as biopsy, endoscopy, bone marrow, and cytoscopy, are invasive tests that often result in considerable discomfort to the patient. Still others, such as CAT scans and MRI scans, are quite expensive and require complex instrumentation.

In particular cancer of the prostate is exclusive to men, and the incidence of prostate cancer increases with age. About 50% of the prostate growth found in men is benign. Among cancerous growths found in patients, about 20% to 30% are found to be low-grade cancers, which could, in men over the age of 70, be left untreated. Therefore, there is a need for a non-invasive technique to discriminate between prostate cancer (CaP) and benign prostate hyperplasia (BPH).

Thus, there is a need for a simple, relatively inexpensive, noninvasive method of screening patients for the presence of cancer, and particularly prostate cancer, that can be used both for preliminary diagnosis or mass screening of patients, and also during treatment to determine whether cancer has gone into remission. Thus, a method for discriminating between benign and malignant prostate tumors solving the aforementioned problems is desired.

SUMMARY OF THE INVENTION

The method for discriminating between benign and malignant prostate tumors relates to analyzing samples of blood, urine and tissue by fluorescence spectroscopy in order to detect the presence of naturally occurring molecules in the fluids and tissue that serve as biomarkers indicative of cancer in the human body. The analysis can be carried out based on fluorescence emission spectra, fluorescence excitation spectra and synchronous (emission and excitation) spectra of bio-samples.

In general, optical analysis of body fluids relates to a method of determining the relative concentration of certain bio-molecules in blood urine and tissue samples by fluorescence spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, flavins (including flavin mononucleotide [FMN], flavin adeno dinucleotide [FAD], and riboflavin), bile components (including biliverdin and bilirubin), tyrosine, tryptophan, and nicotinamide adenine dinucleotide (NADH). The fluorescence spectroscopy techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease, both as a diagnostic screening method and for evaluating the progress of treatment.

The blood samples may be blood plasma and/or extracts from blood cells. The urine samples may be fresh urine samples, or extracts from urine. The tissue may be excised in the form of a small chip (or small chips), or may be left intact inside the body, with the tissue being accessed through an inserted optical fiber. The apparatus used to perform the diagnostic techniques may include either an incoherent light source, such as a lamp, or a coherent light source, such as a laser. The excitation wavelength may be determined by an interference filter, a notch filter, or a grating. The emission intensity may be detected by a photodiode, photomultiplier tube, or CCD array.

The present method for discriminating between benign and malignant prostate tumors using these body fluids and tissue samples can particularly be used to detect the presence of prostate cancer, including identifying early malignant and advanced malignancy stages, and for screening individuals. Particularly, the method utilizes fluorescent intensity bands particularly characteristic of prostate cancer, which are assigned to elastin, collagen, and/or pyridoxine, tryptophan, NADH, flavins, bile pigments and porphyrin. The method further relates to the determination of the significance of these bands in combination with the intensities assigned to the other biomarkers listed above.

BRIEF DESCRIPTION OF THE DRAWINGS

Similar reference characters denote corresponding features consistently throughout the attached drawings.

DETAILED DESCRIPTION OF THE PREFERRED EMBODIMENTS

In general, the method for discriminating between benign and malignant prostate tumors is a method of determining the relative concentration of certain bio-molecules in blood, tissue and urine samples by fluorescence spectroscopy. The relative concentration of these bio-molecules serves as a marker or screening test to assess the presence and stage of cancer in some organ or tissue of the body, and in some cases, the presence of particular types of cancer in the body, particularly cancers originating in the prostate. The bio-molecules include various species of porphyrin, flavin, bile components, and tryptophan, along with structural proteins, such as elastin, collagen, and NADH. The fluorescence spectrography techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease, both as a diagnostic screening method and for evaluating the progress of treatment. The method is further used for discriminating between prostate cancer (CaP) and benign prostate hyperplasia (BPH).

The method may be carried out using any fluorescence spectrography apparatus known in the art. The optical source may be a lamp, such as a halogen lamp, a mercury lamp, a xenon lamp, a tungsten lamp, or other lamp used in fluorescent spectrographs. Alternatively, the optical source may be a coherent light source, such as a diode laser, a helium-cadmium laser, a frequency-doubled, tunable titanium-sapphire laser, or a tunable dye laser. The excitation wavelength may be determined by an interference filter, a notch filter, a slit and grating, or by any other wavelength determining means. Optical detection may be by a photodiode, a photomultiplier tube, an avalanche diode, a CCD array, or any other conventional detector.

Fluorescent spectrography is based upon the principle that certain molecules absorb light at certain frequencies or wavelengths to reach an excited energy level, and subsequently decay to a lower energy state by fluorescing at particular wavelengths. Detectors are capable of detecting this fluorescence with great sensitivity, down to parts in a billion, or even from a single molecule.

The spectral analysis of body fluids and tissue, as set forth herein, rests upon the identification of certain fluorescence excitation-emission wavelengths characteristic of the bio-molecules noted above that may be found in body fluids, such as blood and urine, and in tissue samples. The spectral analysis is further based upon the recognition that the relative proportions of such bio-molecules in blood, tissue and urine are affected by the presence of cancerous conditions in the body and the stage of development of the cancerous condition.

The method for discriminating between benign and malignant prostate tumors can particularly be used to detect the presence of prostate cancer, including identifying early malignant and advanced malignancy stages, along with the screening of individuals (e.g., older men, who are at risk for developing prostate cancer or who are in pre-malignant stages of prostate cancer), and further for discriminating between CaP and BPH in a patient. The present method utilizes analysis of the fluorescent intensity bands particularly characteristic of prostate cancer, which are assigned to elastin, collagen, and/or pyridoxine; tryptophan; flavins; and varying species of porphyrin. The method further relates to the determination of the significance of these bands in combination with the intensities assigned to the other biomarkers listed above. The method will now be explained by reference to particular examples.

EXAMPLE 1

Excised prostate chips were obtained by transurethral surgery from twelve patients. The excised chips roughly measured 10 mm×2 mm×2 mm, and were kept immersed in saline solution. The excised chips were stored in a refrigerator and then carried through spectral analysis within 8 hours of excision. From each patient, a parallel set of samples was taken for conventional histopathology. The following spectral diagnoses are each compared to conventional histopathology diagnoses. Prior to spectral analysis, each sample was washed five times in saline solution, dried on blotting paper, minced and then loaded into a quartz cuvette, which had a 1 mm wide narrow space to hold the solid sample in fixed position. Light from a xenon lamp, of pre-selected wavelength with a size of 2 mm×2 mm, illuminated the tissue samples, thus exciting auto-fluorescence (the auto-fluorescence-based light was detected transverse to the incident light).

Figure 1:
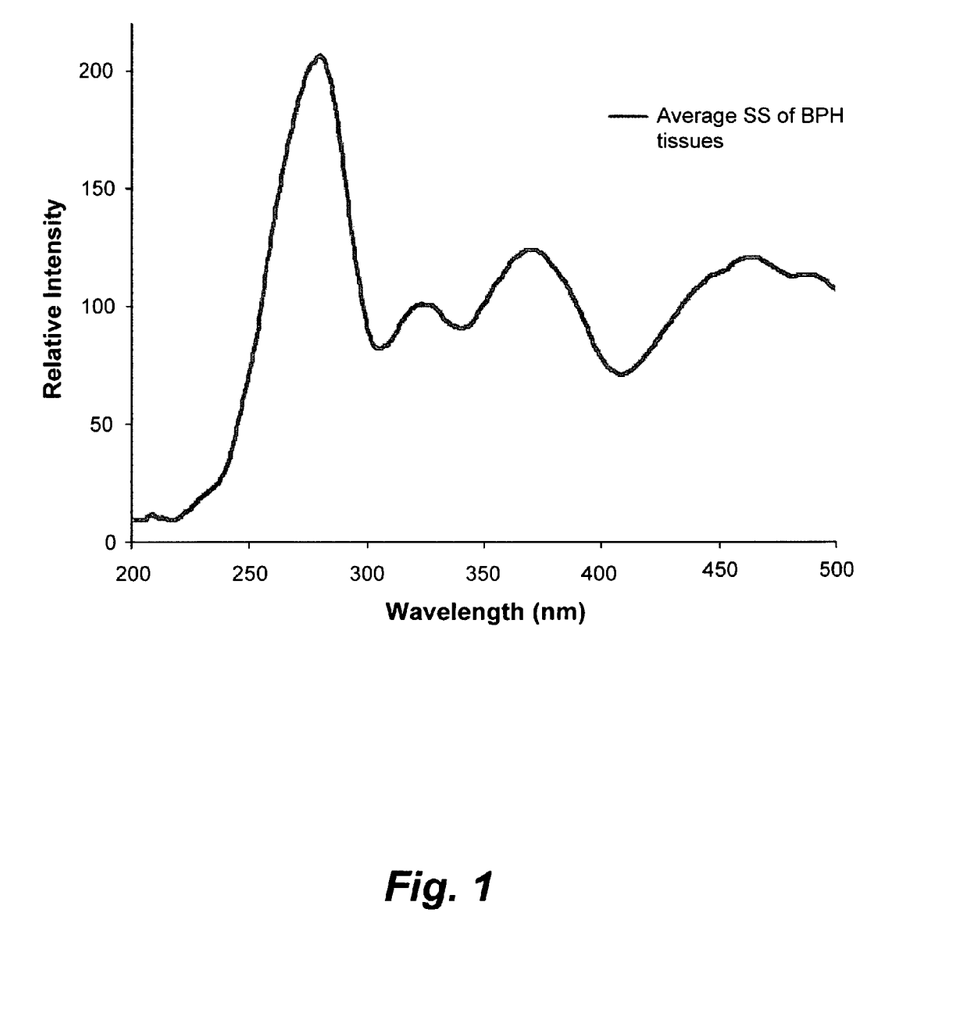
FIG. 1 shows an average of seven synchronous spectra (SS) with an offset of 70 nm for benign prostate hyperplasia (BPH) tissue.

FIG. 1 illustrates the average synchronous spectra (SS) of benign prostate hyperplasia (BPH) as the excitation bands of significant fluorophores, and with the ordinates being relative intensity. As shown, the primary band is found at 280 nm (due to the amino acid tryptophan), with three secondary bands at 327 nm (due to elastin), 385 nm (due to bound NADH), and 450 nm (due to FAD). It should be noted that in fluorescence spectroscopy, it is the relative intensity between the bands that is more important to analysis than the actual intensity of each band. From this point of view, a set of ratio parameters were chosen as $R_1=I_{327}/I_{280}$ (i.e., the ratio between the intensity of the bands at 327 nm and at 280 nm). This ratio is approximately 0.5. Similarly, a second set of ratios $R_2=I_{327}/I_{385}$ is found to be approximately 0.8. A third set of ratios $R_3=I_{327}/I_{450}$ is also found to be approximately 0.8.

Figure 2:
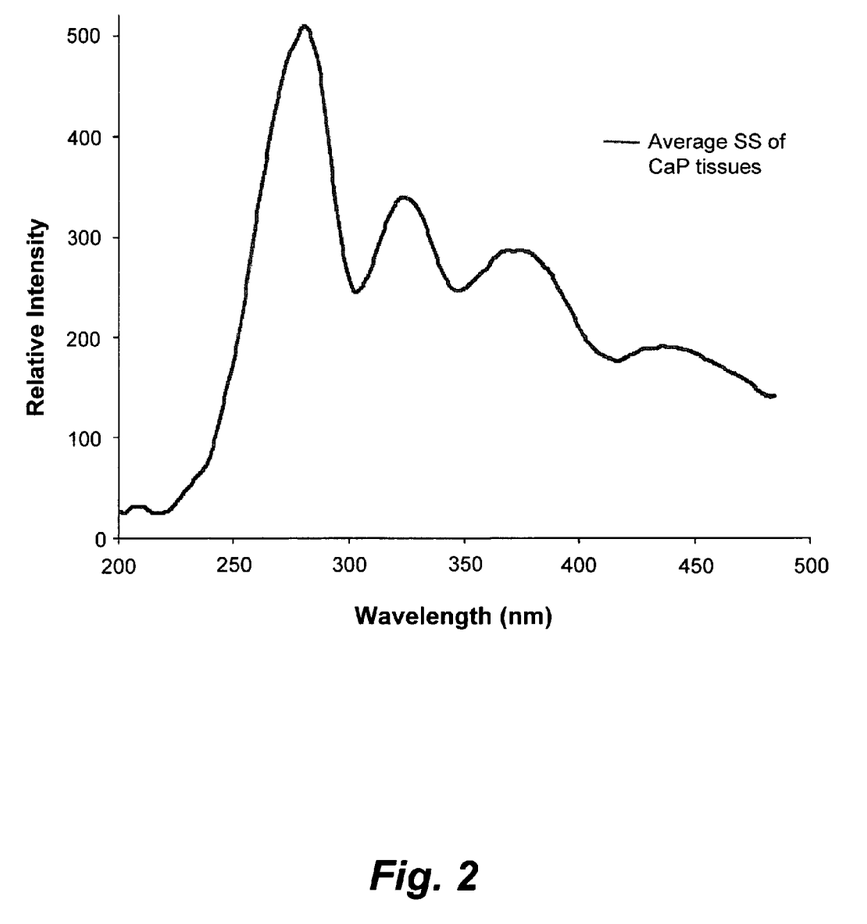
FIG. 2 shows an average of five SS with an offset of 70 nm of prostate cancer (CaP) containing tissue.

FIG. 2 illustrates the average SS of patients with CaP. In FIG. 2, the four bands at 280 nm, 326 nm, 375 nm and 450 nm are also found, as in the case of BPH (shown in FIG. 1). The bands in FIG. 2, however, are out of proportion in malignant tissue, with $R_1$ being approximately 0.64, $R_2$ being approximately 1.26 and $R_3$ being approximately 2. It should also be noted that the intensity of all of the bands is about two to three times greater for malignant tissue in comparison with benign tissue.

Figure 3:
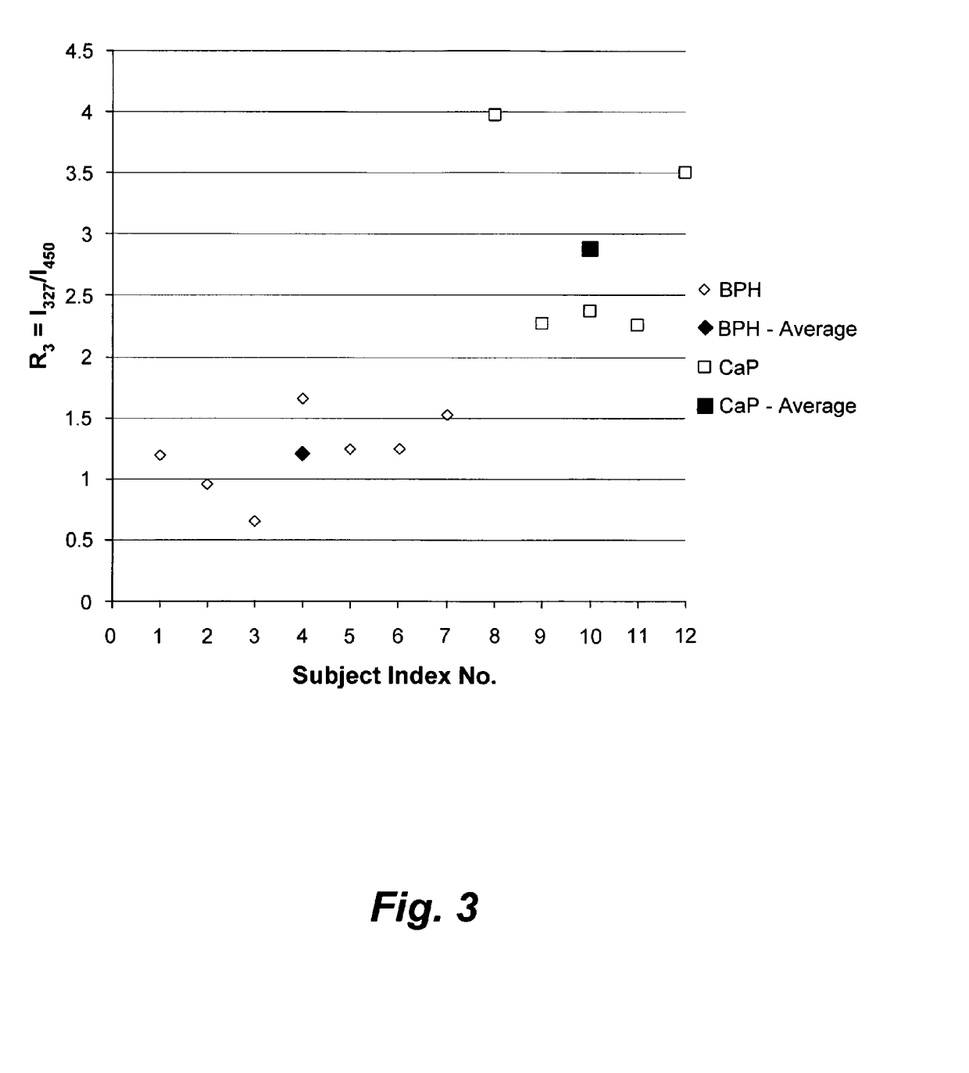
FIG. 3 is a scatter plot illustrating a comparison between the BPH and CaP analyses of FIGS. 1 and 2, respectively, illustrating a particular ratio parameter $R_3$.
Figure 4:
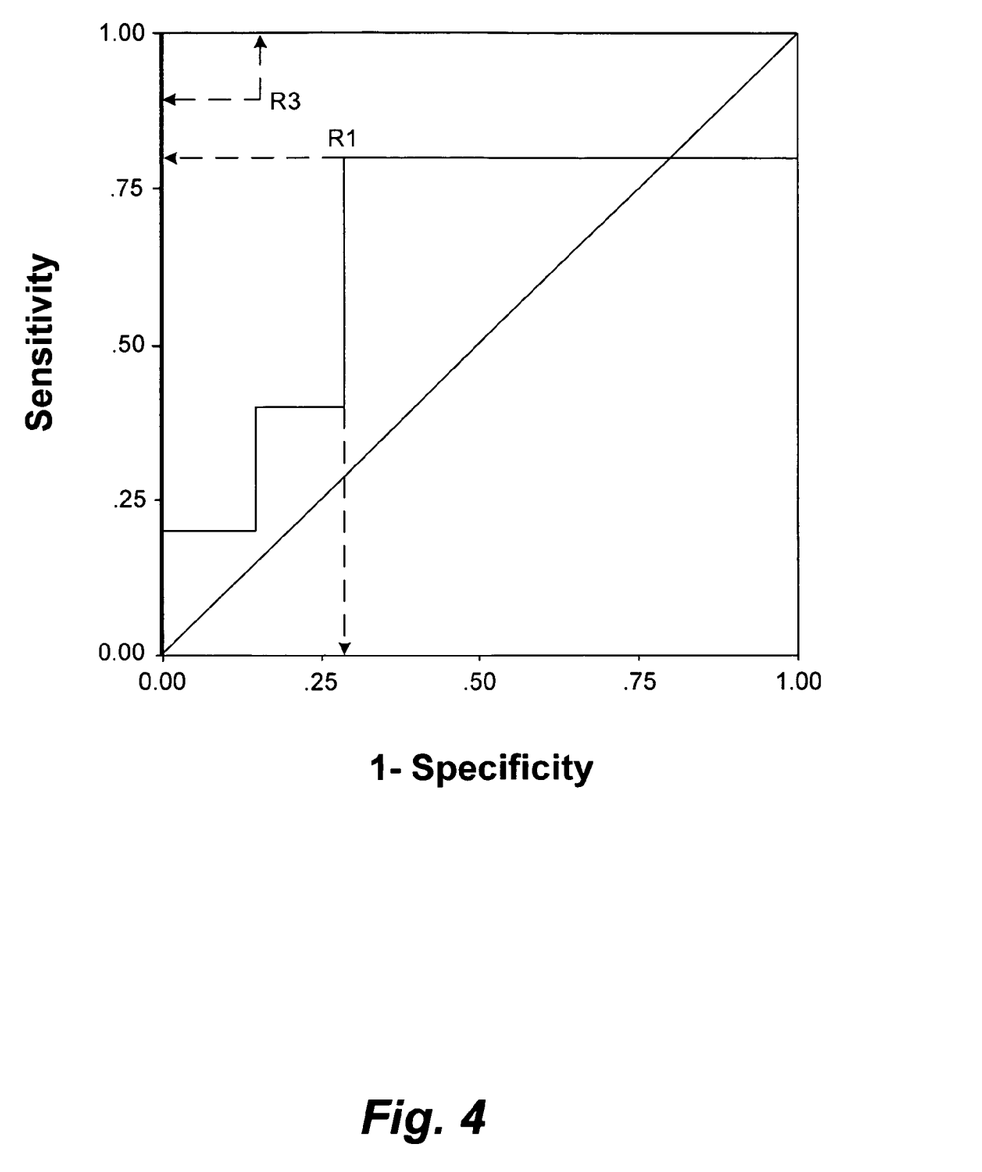
FIG. 4 is a ROC curve illustrating approximately 100% specificity and sensitivity in the analyses of FIGS. 1 and 3.

These ratio parameters vary from one sample to another, and the actual ratios for seven benign and five malignant prostate tumors are listed in Table 1 below. A scatter plot, shown in FIG. 3, for the ratio $R_3$, indicates that the two groups are clearly separated out. FIG. 4 illustrates a ROC (receiver operator characteristics) curve for the ratio parameter $R_3$, showing that the classification of the two groups (i.e., benign and malignant) is possible with sensitivity and specificity, each being approximately 100%. It should be noted that the ROC curve for $R_3$ is an inverted "L" (shown with a dashed line in FIG. 4). The ROC curve for $R_1$, on the other hand, is a step-like line. For ratio $R_1$, for a specificity of 72%, the sensitivity is only 78% (as shown by the arrows in FIG. 4).

Figure 7:
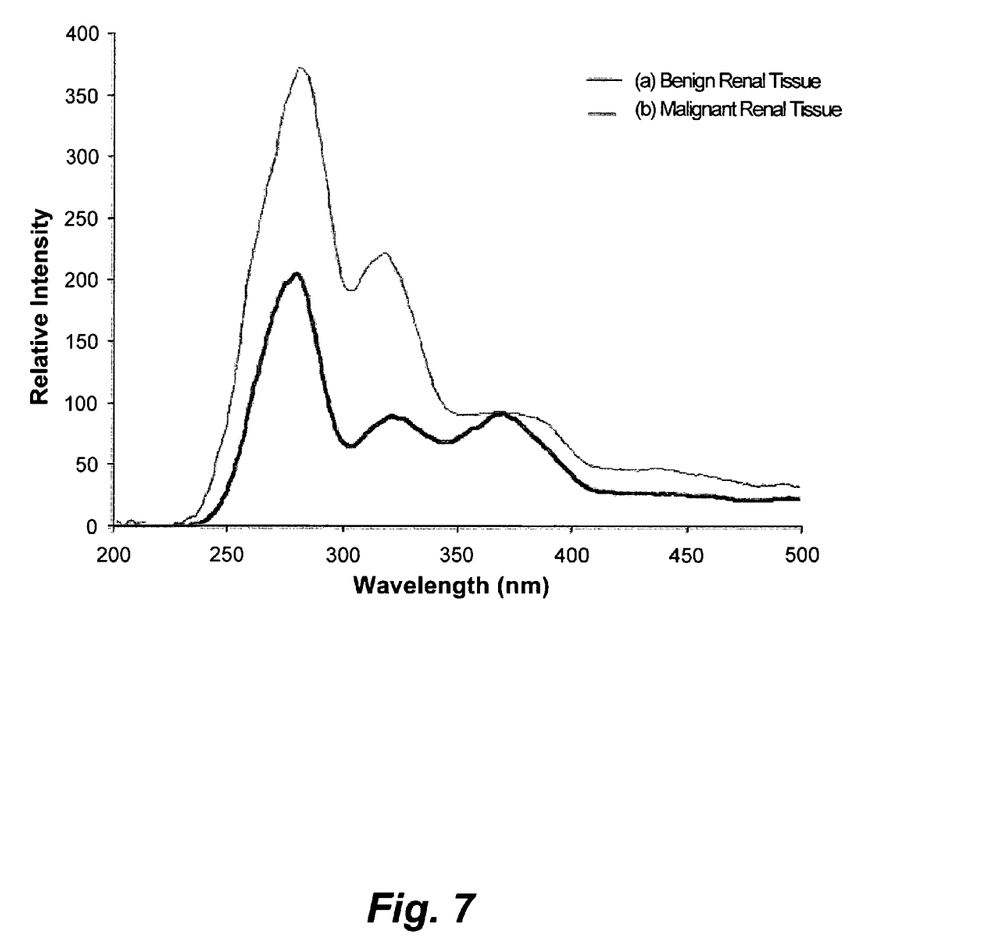
FIG. 7 shows the SS of benign and malignant renal tissue.

It is important to emphasize that the above spectral features of benign and malignant conditions are not exclusive to prostate tissue. Tissues of other organs also exhibit similar trends, as shown by line (a) in FIG. 7 for benign renal tissue and by line (b) for malignant renal tissue. For benign renal tissue, $R_1$ is approximately 0.4, $R_2$ is approximately 0.8, and $R_3$ is approximately 2. For malignant renal tissue, $R_1$ is approximately 0.7, $R_2$ is approximately 3, and $R_3$ is approximately 4. The band at 327 nm grows out of proportion as malignancy sets in on many organs (such as, for example, the lungs, colon, breasts, kidney, bladder, and rectum).

EXAMPLE 2

A disposable syringe was used to uptake 5 ml of venous blood from a subject. The blood was placed in a sterile vial containing ethylenediaminetetraacetic acid (EDTA) anticoagulant. The blood was then centrifuged at 4,000 rpm for 15 minutes, and the supernatant plasma was separated out and collected in a sterile vial. The formed elements, containing mostly cells, such as erythrocytes, were then treated with acetone in a ratio of 1:2 (i.e., 1 ml of formed elements to every 2 ml of acetone). The sample was vigorously shaken 100 times and then centrifuged again at 4,000 rpm for 15 minutes.

The supernatant obtained was a clear solution containing the bio-molecules used as tumor markers. These were subjected to the spectral analysis described before. The wavelength of excitation was fixed at 400 nm by adjusting the interference filter or grating, and the fluorescence emission spectrum was obtained in a range of 425 to 720 nm.

Figure 8:
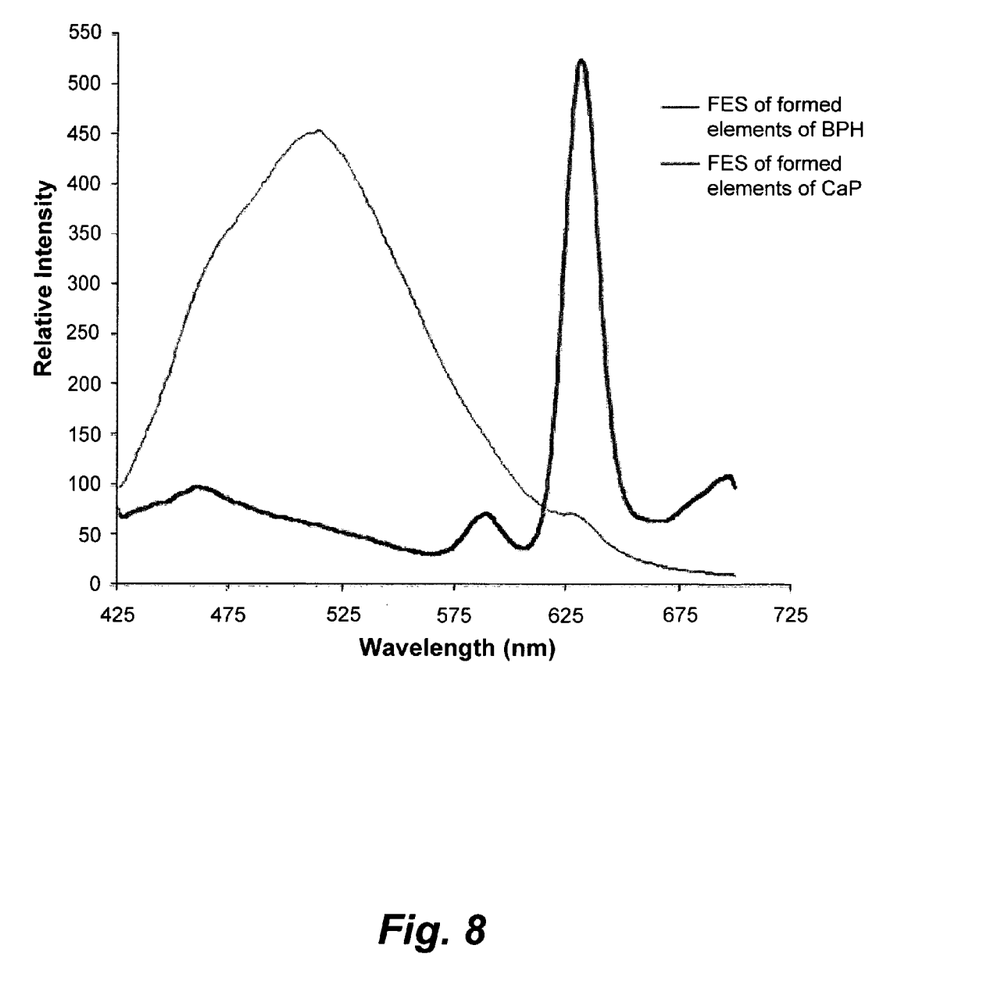
FIG. 8 shows the FES at an excitation wavelength of 400 nm of a sample extract of formed elements of blood of a person with BPH compared with a CaP patient.

A typical result from this analysis is shown in FIG. 8 for a sample from a patient with BPH compared with a sample from an individual with CaP. The spectrum consists of four bands: the first at around 460 nm, due to Raman scattering of acetone; the second being a fluorescence band at around 525

TABLE 1

| Ratio Parameter | BPH | | | | | | | Malignant Prostate | | | | |
|---|---|---|---|---|---|---|---|---|---|---|---|---|
| $R_1$ | 0.58 | 0.72 | 0.56 | 0.54 | 0.51 | 0.91 | 0.4 | 0.76 | 0.65 | 0.36 | 0.7 | 0.92 |
| $R_2$ | 0.91 | 0.93 | 0.65 | 1.07 | 1.05 | 1.2 | 0.86 | 1.7 | 1.23 | 1.42 | 1.36 | 2.25 |
| $R_3$ | 1.19 | 0.95 | 0.65 | 1.65 | 1.24 | 1.24 | 2.22 | 3.98 | 2.27 | 2.37 | 2.25 | 3.5 |

Figure 5:
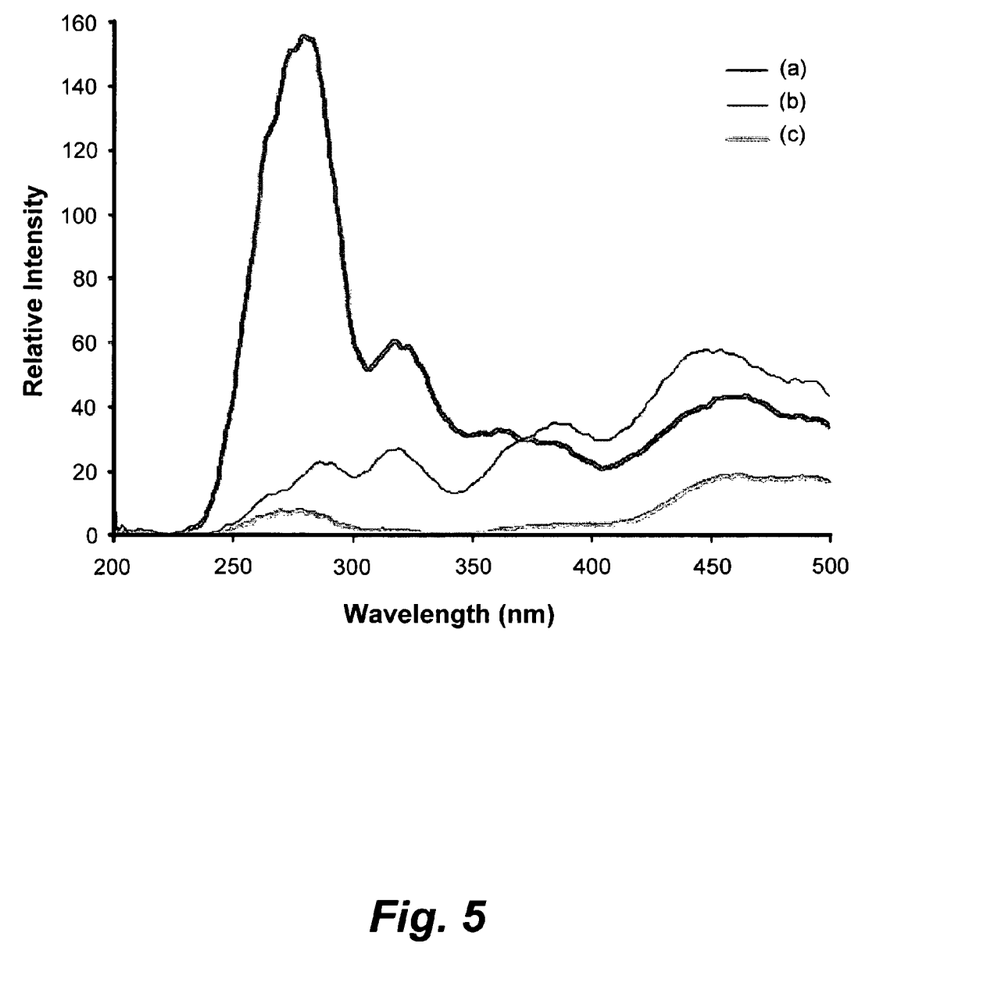
FIG. 5 shows the synchronous spectra (SS) for CaP, with measurements being taken at varying distances.

In FIG. 5, line (a) illustrates the SS of a CaP tissue sample, which has all of the features of malignancy, with $R_2>1.3$ and $R_3>1.4$. From this segment of tissue, this spectral diagnosis would have classified the tissue as malignant. Lines (b) and (c) in FIG. 5 show the synchronous fluorescent excitation spectra (SS) of the same prostate cancer tissue, but 3 mm away from the position excited above. Here, $R_2<1.3$ and $R_3<1.4$, so that this part of the tissue exhibits the features of benign neoplasia. Only one such example is shown here to indicate that the tissue can be analyzed with good spatial resolution to delineate between the benign and malignant domains.

Figure 6A:
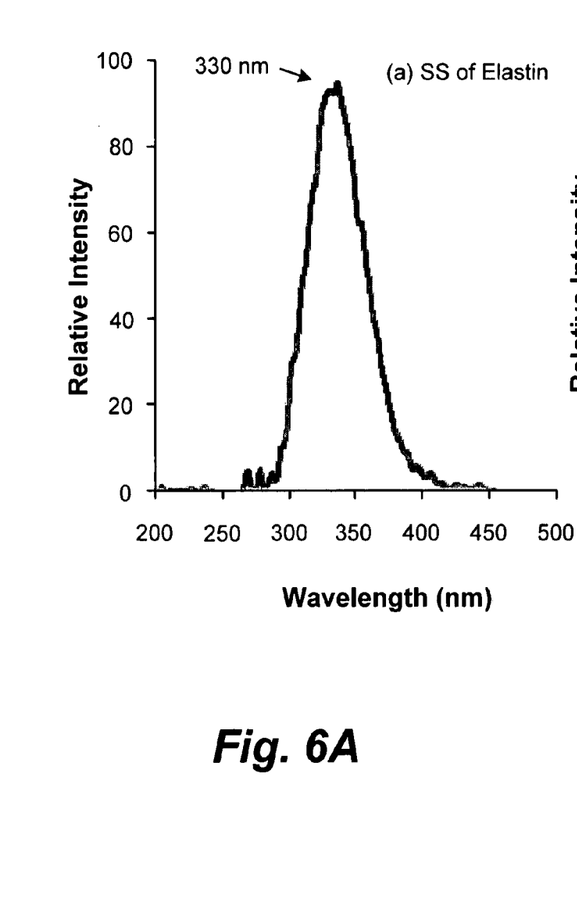
FIG. 6A shows the SS of elastin in phosphate buffered saline (PBS).
Figure 6B:
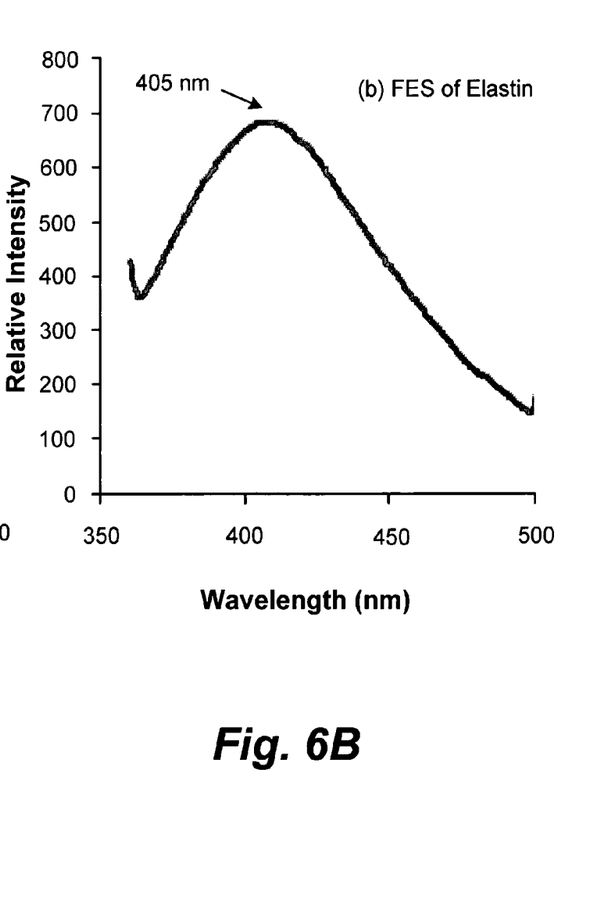
FIG. 6B shows the fluorescence emission spectra (FES) of elastin in PBS.
Figure 6C:
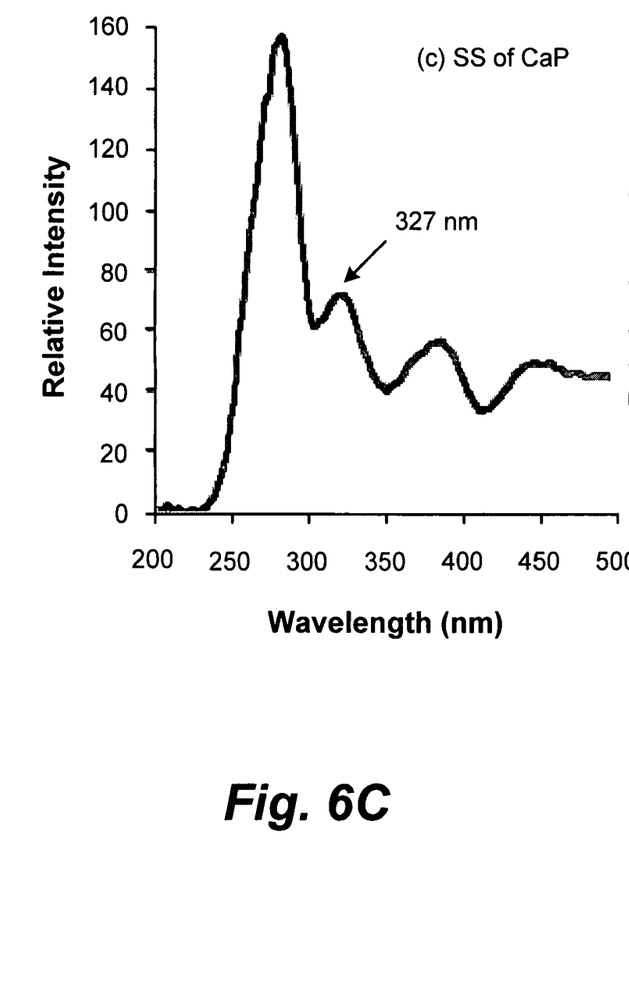
FIG. 6C shows the synchronous spectra (SS) of tissue of a CaP patient.
Figure 6D:
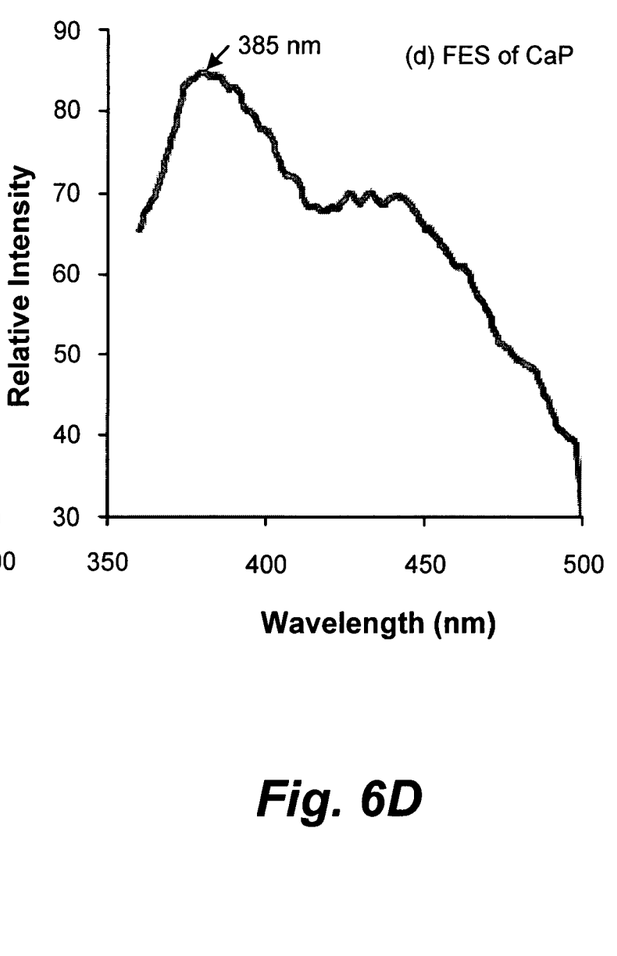
FIG. 6D shows the FES of the tissue of the CaP patient of FIG. 6C.

As most of the above results are based on the ratio of all peaks with respect to the peak at 327 nm (due to elastin), FIG. 6A is provided to illustrate the SS of a sample of elastin, and FIG. 6B is provided to illustrate the fluorescence emission spectrum (FES) of the same sample of elastin excited at 325 nm, which is the SS peak of elastin. It can be seen that 327 nm in SS and 390 nm in FES are a matched pair, providing a unique signature for the structural protein elastin. FIG. 6C and FIG. 6D are a similar set of SS and FES of prostate cancer tissue. There is a one-to-one correspondence between the SS and FES set of elastin and that of prostate cancer.

nm (most likely due to riboflavin and bile components); the third being a fluorescence band at around 585 nm due to anionic species of porphyrin; and the fourth being a fluorescence band at around 630 nm due to neutral species of porphyrin.

The intensities of the bands were measured and denoted as $I_{460}$, $I_{520}$, $I_{585}$ and $I_{630}$, respectively. The ratios of the intensities are denoted as $R_4$ and $R_5$, as above. In this example, $R_4=I_{630}/I_{585}$. If $R_4<1$, then the patient is diagnosed with BPH. If $1.5>R_4>3$, then the patient is diagnosed with a low grade CaP. If $R_4>3$, then the patient is diagnosed with high grade CaP. The ratio $R_5$ is defined as $R_5=I_{630}/I_{525}$. If $R_5<0.5$, then the patient is diagnosed with BPH. If $1.5>R_5>2$, then the patient is diagnosed with a low grade CaP. If $R_5>2$, then the patient is diagnosed with a high grade CaP.

$R_4$ and $R_5$ depend upon the concentration of porphyrin, a bio-molecule involved in heme metabolism, and flavin. Porphyrin is found at higher concentrations in the tissue of cancer patients than in BPH subjects due to the abnormal cell proliferation in cancer patients. This is, in general, the basis for laser-based photodynamic therapy, which is in practice all over the world.

The present method is particularly concerned with the concentration of porphyrin carried from the tissue into the blood stream and excreted through urine. If the concentration of this fluorophore is higher, then the tumor activity or the tumor volume is also higher.

EXAMPLE 3

Figure 9:
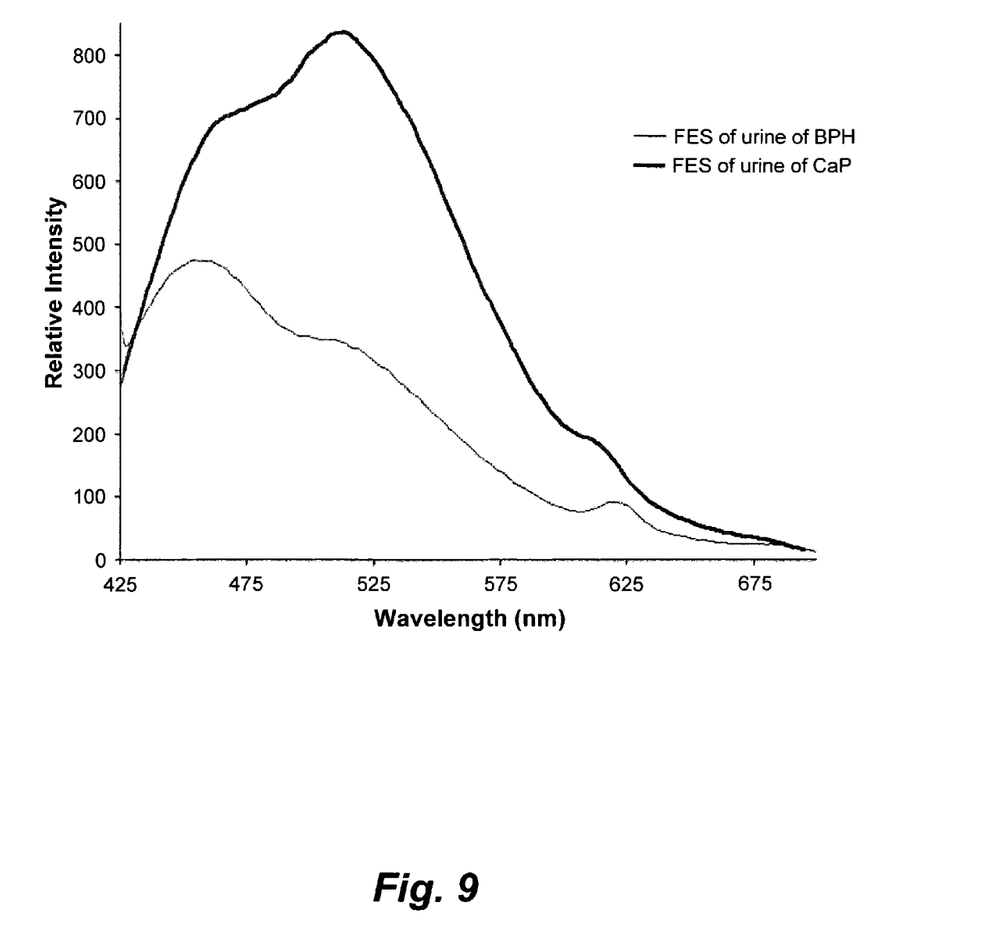
FIG. 9 shows the FES at an excitation wavelength of 400 nm of a urine sample of a CaP patient compared to that of a person with BPH.

Urine samples were prepared for analysis in this example. The subject was required to provide the first voided urine in a sterile vial after 48 hours of strict abstinence from non-essential medicines (including herbal and ayurvedic treatments), spicy meals and meats. 2 ml of urine was dropped in a quartz cuvette. The excitation wavelength was set at 400 nm, and the fluorescence spectrum from 425 to 700 nm was obtained. Exemplary spectra for a BPH patient and a prostate cancer patient are shown in FIG. 9. The 470 nm, 520 nm and 620 nm bands are of interest in this analysis, corresponding, respectively, to intensity maxima for NADH, flavins and porphyrin. A set of cancer-defining ratio parameters are given below in Table 2:

TABLE 2

Ratio Parameters $R_3$ and $R_4$

| Ratio parameter | BPH | Low Grade CaP | High Grade CaP |
|---|---|---|---|
| $R_6 = I_{520}/I_{470}$ | <0.75 | 0.8-1 | <1.2 |
| $R_7 = I_{620}/I_{470}$ | ≦0.2 | 0.2-0.3 | >0.3 |

EXAMPLE 4

Fluorescence excitation spectra of the samples were obtained with a fixed emission grating and a rotated excitation grating. The excitation spectra are found to be similar to, but not identical to, the absorption spectra. This may be modified to obtain the synchronous spectra (SS). In this example, the excitation grating and emission grating were set at a wavelength difference of 70 nm, as required for the specific analysis (i.e., when one grating was set at 200 nm, the other was set at 270 nm, with the offset wavelength difference being 70 nm). Then, both gratings were synchronously scanned. The fluorescence obtained with the excitation at 200 nm was collected from 270 nm onwards. Next, the excitation grating was moved to 210 nm and, synchronously, the emission grating was moved to 280 nm, collecting fluorescence. This type of synchronous scanning may be applied up to 600 nm.

This provides a compounded spectrum of fluorescence emission and excitation bands of many molecules, but with each molecule being excited individually. This process provides better resolution and identification of weakly fluorescing, submerged fluorophores, thus providing an additional window of analysis.

Figure 10:
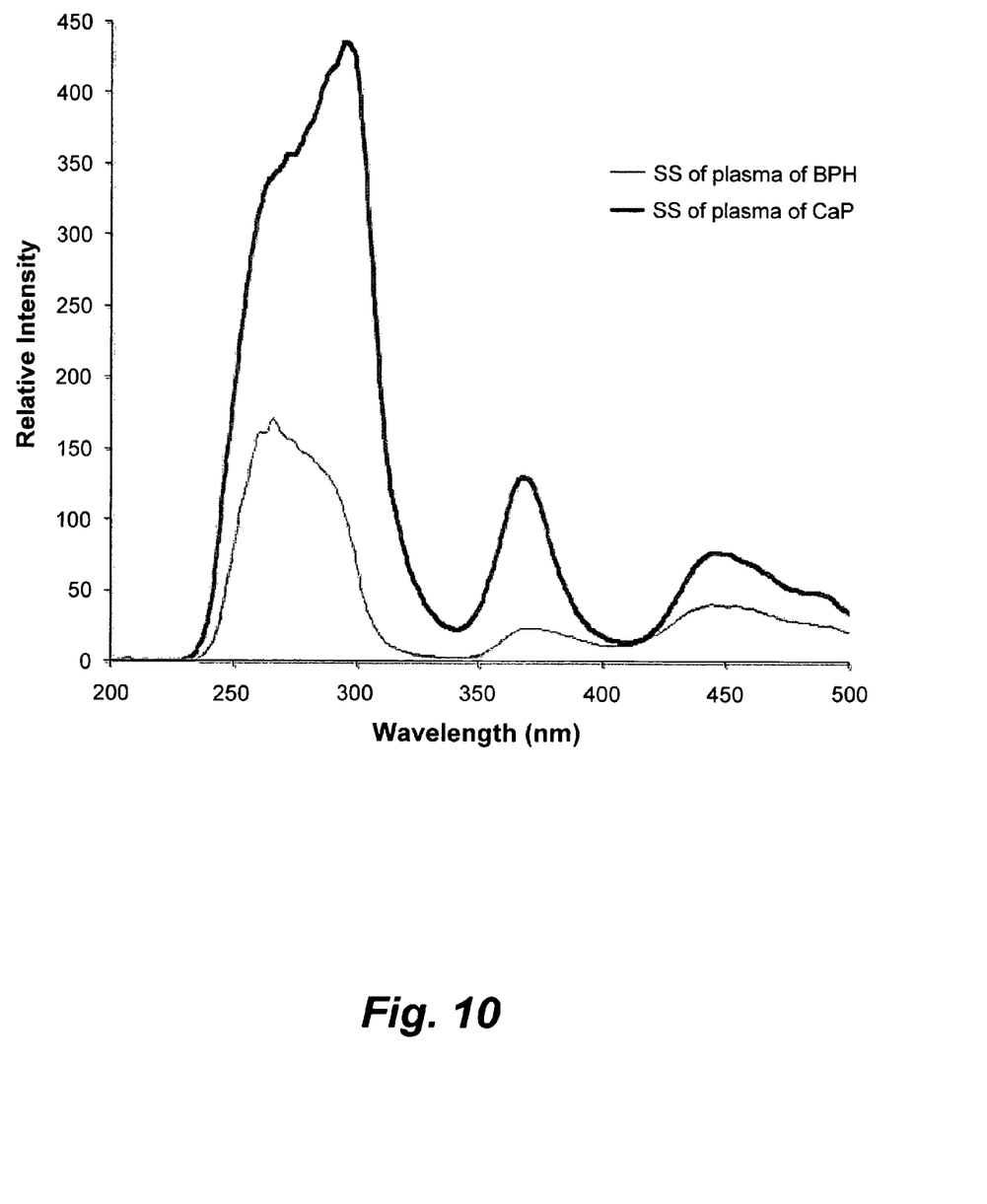
FIG. 10 shows the SS with an offset of 70 nm of a blood plasma sample of a person with BPH compared with that of a CaP patient.

Blood plasma samples were prepared and placed in a cuvette for spectral analysis. Spectra obtained for these samples showed distinct and marked differences between healthy and diseased body fluid. With reference to the SS of blood plasma, with an offset of 70 nm (as shown in FIG. 10), there were well-defined bands at around 290 nm, 365 nm, and 450 nm, with a shoulder at 270 nm. Since blood plasma contains a host of free and enzyme-bound fluorophores (i.e., bio-molecules), bands may only tentatively be assigned to the fluorophores. Out of these, the 290 nm band is due tryptophan, the 365 nm band is, most likely, due to NADH, and the 450 nm band is due to flavins. Comparing the benign and malignant spectra, it can be seen that these bio-molecules are out of proportion in diseased blood plasma, as shown in the comparison spectra of FIG. 10. For example, the ratio $R_8 = I_{290}/I_{270}$ is approximately 0.8, indicating BPH, but is found to be approximately 1.2 for the patient with CaP. An additional ratio $R_9 = I_{290}/I_{340}$ provides a measure of intensity representing the quantity of tryptophan, which is 22 for CaP, but only 15 for BPH. Further, the ratio $R_{10} = I_{365}/I_{450}$ is found to be about 0.5 for BPH and 2 for a CaP patient.

It is to be understood that the present invention is not limited to the embodiments described above, but encompasses any and all embodiments within the scope of the following claims.

We claim:

1. A method for discriminating between benign and malignant prostate tumors, comprising the steps of:
   irradiating a tissue sample from a patient with light from an optical source;
   detecting fluorescence from the tissue sample;
   identifying and measuring fluorescence intensity maxima in a set of synchronous spectra corresponding to species of tryptophan, elastin, bound and free NADH, and flavins;
   defining a first ratio $R_1$ as the ratio between the intensity maximum of the excitation band corresponding to elastin and the intensity maximum of the excitation band corresponding to tryptophan;
   defining a second ratio $R_2$ as the ratio between the intensity maximum of the excitation band corresponding to elastin and the intensity maximum of the excitation band corresponding to NADH;
   defining a third ratio $R_3$ as the ratio between the intensity maximum of the excitation band corresponding to elastin and the intensity maximum of the excitation band corresponding to flavins;
   diagnosing the patient as having benign prostate hyperplasia when the ratio $R_1$ is approximately 0.5, the ratio $R_2$ is approximately 0.8 and the ratio $R_3$ is approximately 0.8; and
   diagnosing the patient as having prostate cancer when the ratio $R_1$ is at least approximately 0.64, the ratio $R_2$ is at least approximately 1.26 and the ratio $R_3$ is at least approximately 2.0.

* * * * *